United States Patent [19]
Newman et al.

[11] Patent Number: 5,201,748
[45] Date of Patent: Apr. 13, 1993

[54] RETRACTABLE-BLADED SURGICAL SCALPEL

[76] Inventors: Philip H. Newman, 98 Rim Rd.; B. Michael Jackson, 3917 West Rd.; Charles T. Gregg, 424 Kiva; David Platts, 1932-B 42nd St., all of Los Alamos, N. Mex. 87544

[21] Appl. No.: 891,756

[22] Filed: Jun. 1, 1992

[51] Int. Cl.⁵ .............................................. A61B 17/32
[52] U.S. Cl. .................................. 606/167; 30/151; 30/335
[58] Field of Search ............... 606/167, 172, 181, 182, 606/185; 30/151, 162, 164, 167, 286, 335; 128/751

[56] References Cited
U.S. PATENT DOCUMENTS

| | | |
|---|---|---|
| 2,735,176 | 2/1956 | Costin . |
| 3,025,598 | 3/1962 | Nissen .................................. 30/162 |
| 3,657,812 | 4/1972 | Lee . |
| 3,905,101 | 9/1975 | Shepherd . |
| 4,091,537 | 5/1978 | Stevenson, Jr. ...................... 30/151 |
| 4,523,379 | 6/1985 | Osterhout et al. .................... 30/151 |
| 4,663,846 | 5/1987 | Takayama ............................. 30/162 |
| 4,805,304 | 2/1989 | Knoop . |
| 4,884,569 | 12/1989 | Fedorov et al. ...................... 606/166 |
| 4,949,458 | 8/1990 | Davis et al. ........................... 30/162 |
| 5,071,426 | 12/1991 | Dolgin et al. . |

FOREIGN PATENT DOCUMENTS
3722899 1/1989 Fed. Rep. of Germany ...... 606/167

*Primary Examiner*—John D. Yasko
*Assistant Examiner*—William W. Lewis
*Attorney, Agent, or Firm*—Samuel M. Freund

[57] ABSTRACT

A surgical scalpel having a replacable, retractable cutting blade which may be locked in the operating or deployed position using a single digit on one hand is described. Safety of hospital personnel and medical waste disposal personnel is achieved without loss of function or convenience of the scalpel.

5 Claims, 4 Drawing Sheets

RETRACTABLE-BLADED SURGICAL SCALPEL

BACKGROUND OF THE INVENTION

The present invention relates generally to surgical cutting instruments, and more particularly to surgical scalpels having retractable blades.

It is well known that existing surgical cutting implements provide a significant potential for harm to surgeons and support personnel. That is, with attention directed toward the patient, rapid handling of surgical instruments with exposed sharp edges occasionally leads to cuts and puncture wounds, and more often to loss of integrity of surgical gloves. With increasing risk of life-threatening infectious diseases, it is imperative that such risks be minimized.

Utility knives having retractable blades are well known. For example, U.S. Pat. No. 4,805,304 for "Utility Knife Having A Sliding Blade Holder," which issued to Heinz-Pete Knoop on Feb. 21, 1989, describes a knife with a substantially hollow handle having a knife blade guided longitudinally in a knife blade guide track and at least one slider member coupled with the handle side of the longitudinally movable knife blade. The slider member penetrates a wall of the handle in a slider member longitudinal slot in the handle broad side. The slot opens at both broad sides. The slider member has on each of the handle broad sides an operating piece engageable by a thumb. Both of the operating pieces receive between themselves and the knife blade at least one guide strip extending parallel to the handle longitudinal axis. The slider member is spring loaded for retraction and requires continuous thumb operation unless a locking device is employed. Thus, if the thumb is removed and a locking device is not employed, the knife blade is automatically pulled back into the knife handle.

Similarly, surgical knives have been described wherein various types of blade protection is available. U.S. Pat. No. 3,905,101 for "Disposable Surgical Scalpel," issued to John W. Shepherd on Sept. 16, 1975. Therein is described a single, monassembly, disposable surgical scalpel which includes a handle, a cutting blade attached to the handle, a sheath movably attached to the handle, means for releasably locking the sheath whereby the blade is sheathed, and means for releasably locking the sheath in a position which exposes the blade. Although the sheathable instrument taught by Shepherd would achieve the desired increase in safety for operating room personnel, two hands are required to operate the locking mechanism, thereby rendering the instrument considerably more cumbersome to use than conventional scalpels.

Similarly, for U.S. Pat. No. 2,735,176 for "Veterinary Surgical Knife," which issued to William J. Costin on May 22, 1953. Therein is described a surgical knife which includes a hollow ground blade of surgical steel and a hollow handle into which the blade can be fully retracted for protection while the blade is not in use and from which the edged portion of the blade can be projected for use with the blade disposed substantially in longitudinal alignment with the handle. The locking mechanism taught includes a threaded pin attached to the blade which extends through a slot in the handle, and a knob which is threaded onto the pin for locking the blade in either an extended or withdrawn position. Two hands are required for successful operation of the Costin invention.

Accordingly, it is an object of the present invention to provide surgical scalpels having retractable blades which may be locked in either a deployed or a retracted position.

Another object of our invention is to provide surgical scalpels having retractable blades which may be locked in either a deployed or a retracted position and which may be operated using one digit of one hand.

Yet another object of the invention is to provide surgical scalpels having retractable blades which may be locked in either a deployed or retracted position, but which cannot accidentally be deployed.

Still another object of our invention is to provide surgical scalpels having retractable blades for which blades may be changed during a surgical procedure.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention, as embodied and broadly described herein, the retractable-blade surgical scalpel of this invention includes a generally flat, elongated handle having two generally flat sides, each having an interior flat recessed inner surface which together form an elongated cavity within the handle extending over its long dimension and opening to the outside at the blade end, one side having two windows, the window closest the blade end being elongated along the long dimension of the handle, the other side of the handle having an interior elongated slot which terminates before reaching the blade end of the handle and opening into the cavity toward the slotted side of the handle, the cavity and the interior slot both opening to the outside at the end of the handle away from the blade; a surgical cutting blade; a flat, elongated slide member adapted to move horizontally through the cavity in the handle for holding the surgical cutting blade and having a portion adapted to be engaged by and actuated by a single digit of one hand through the elongated window in the side of the handle member, having a raised, deformable latch in the region of the slide member away from the end which holds the blade and on the side thereof having the digit-engaging portion, and having a tab portion disposed perpendicular to the flat dimension of the slide in a direction away from the digit-engaging portion adapted to slidably move in the interior slot in one side of the handle; and a coil spring located within the interior slot in one side of the handle along the long dimension thereof and adapted to continuously contact the tab portion of the slide, thereby providing a force on the slide directed away from the blade end thereof; whereby the blade may be reversibly locked either entirely within the handle or extend outside thereof through the opening therein in the blade end thereof for use in surgical procedures without continuous contact being required with the digit-engaging portion when the slide is moved sufficiently away from the blade end of the handle to permit the raised, deformable latch to extend through the window located away from the blade end of the handle and counteract the action of the coil spring, or when the slide is moved sufficiently toward the blade end of the handle to permit the raised, deformable latch to extend through the window closest to the blade end of the handle and counteract the action of the coil spring, respectively, and whereby the slide may be reversibly removed for replacement with a fresh blade and slide assembly when the raised, deformable latch is depressed in the window furthest from the blade end of the handle and the slide is moved away from the blade end thereof.

Benefits and advantages of the present surgical scalpel invention include direct, single digit/single-handed operation, blade stability, either in the extended or retracted positions, and certain, readily-obtainable protection for personnel in the operating room and personnel involved in hospital waste disposal since the blade thereof cannot accidentally be deployed.

BRIEF DESCRIPTION OF THE DRAWINGS

The accompanying drawings, which are incorporated in and forms a part of the specification, illustrate two embodiments of the present invention and, together with the description, serve to explain the principles of the invention.

DETAILED DESCRIPTION OF THE PREFERRED EMBODIMENTS OF THE INVENTION

Briefly, the present invention includes a surgical scalpel having a retractable blade which may be locked in the operating or deployed position using a single-digit on one hand.

Figure 1A:
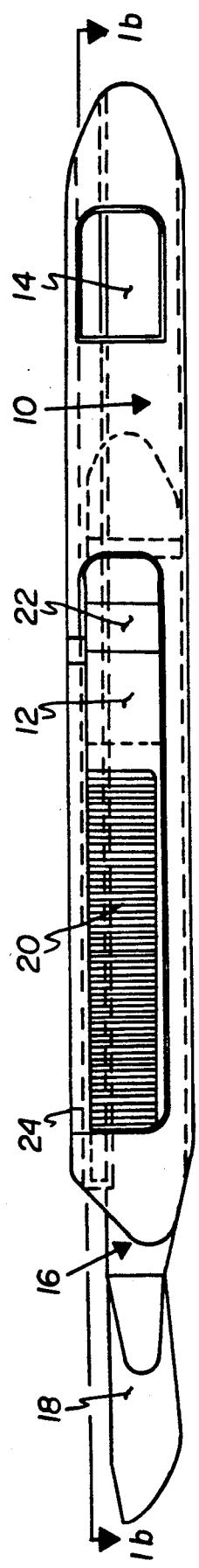
FIGS. 1a-e show a schematic representation of the side, top, and rear views of the assembled scalpel of the present invention and illustrates the handle, slide and blade in the locked, cutting (deployed) position. The rear view illustrates the handle cavity within which the slide moves, the internal elongated slot in one side of the handle in which the restoring coil spring is located, and the coil spring-engaging tab of the slide.
Figure 1B:
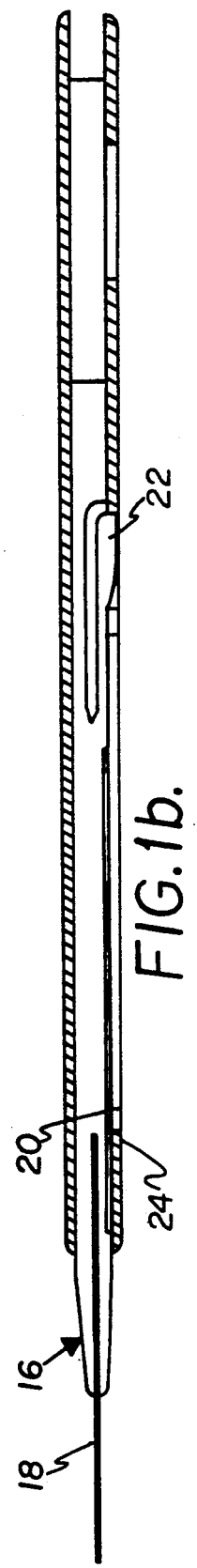
Figure 1C:
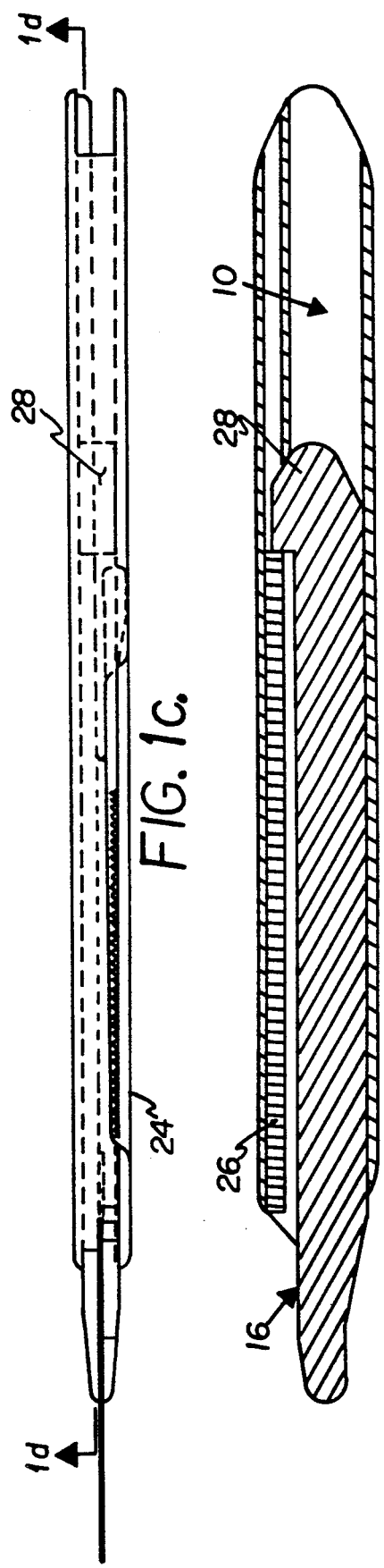
Figure 1D:
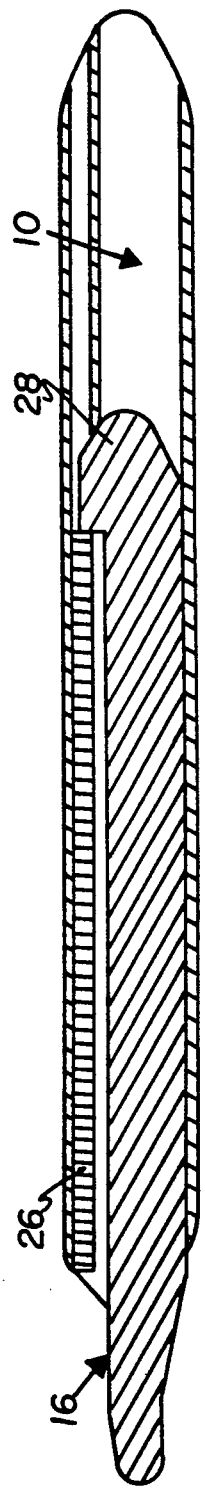
Figure 1E:
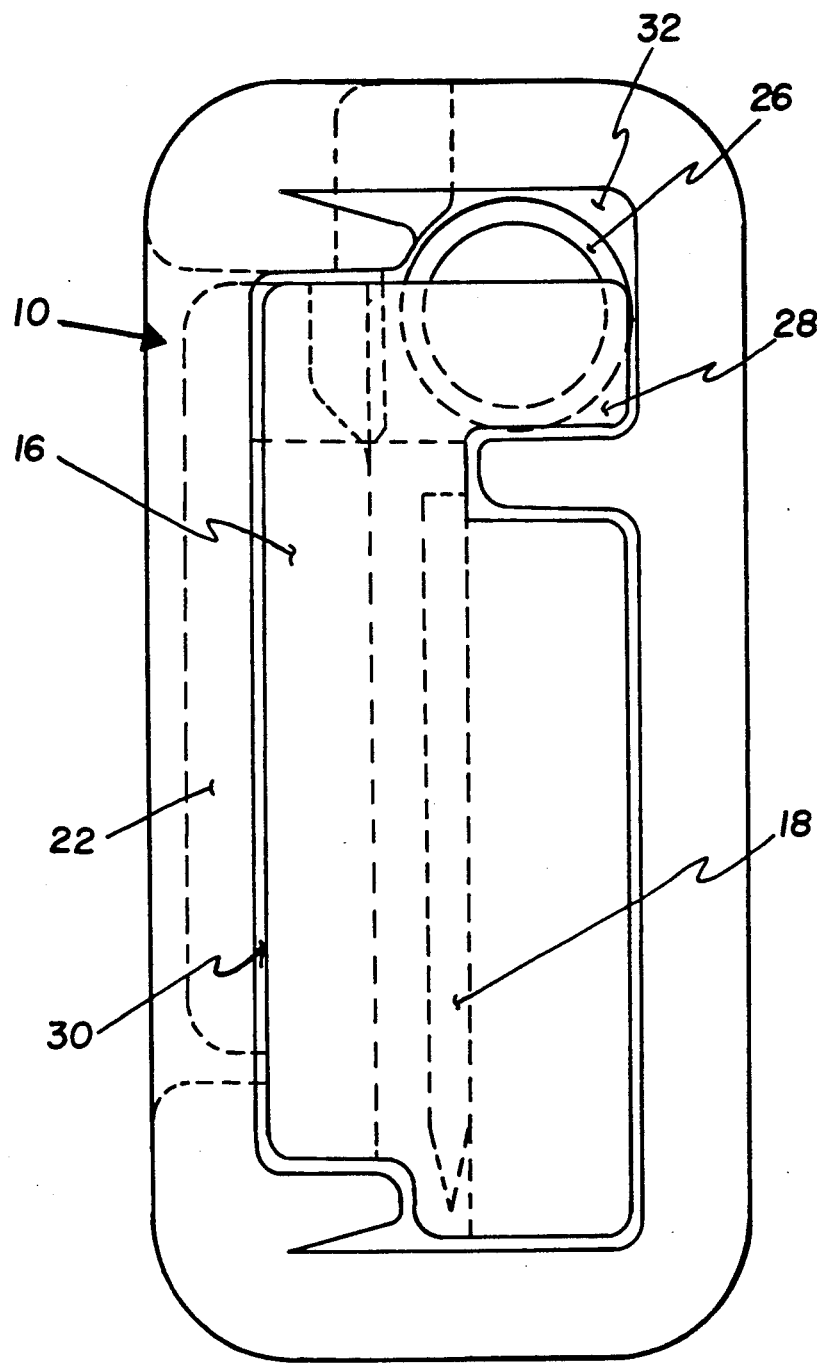
Figure 2A:
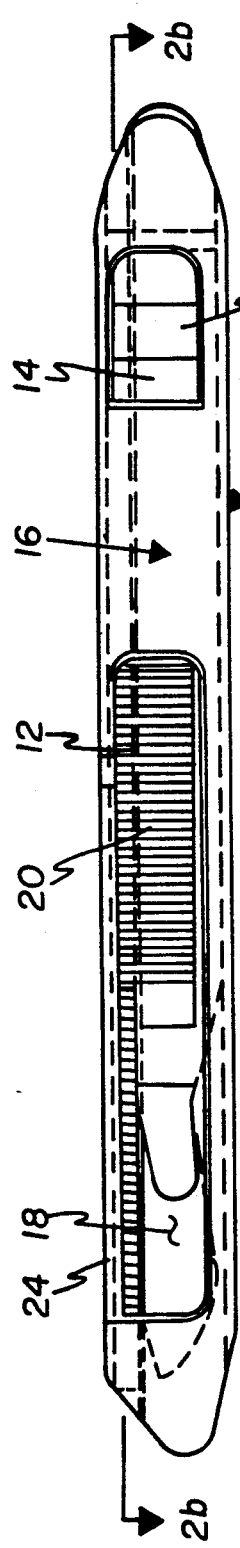
FIGS. 2a-c show a schematic representation of the side and top views of the assembled scalpel and illustrates the handle, slide and blade in the locked, retracted safety position.
Figure 2B:
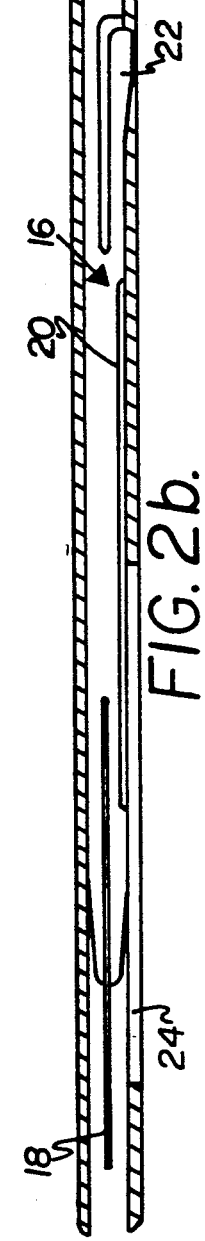
Figure 2C:
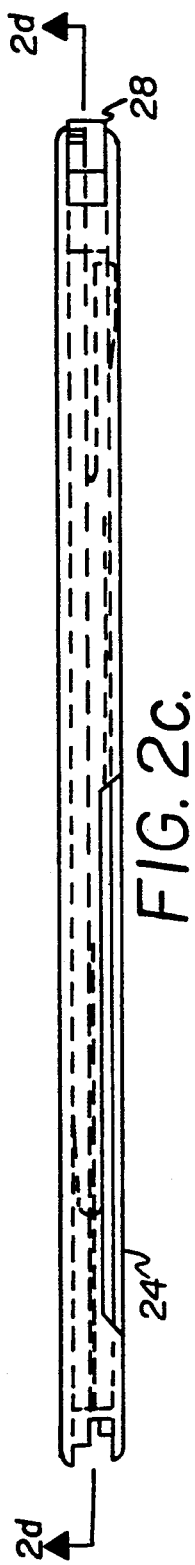
Figure 2D:
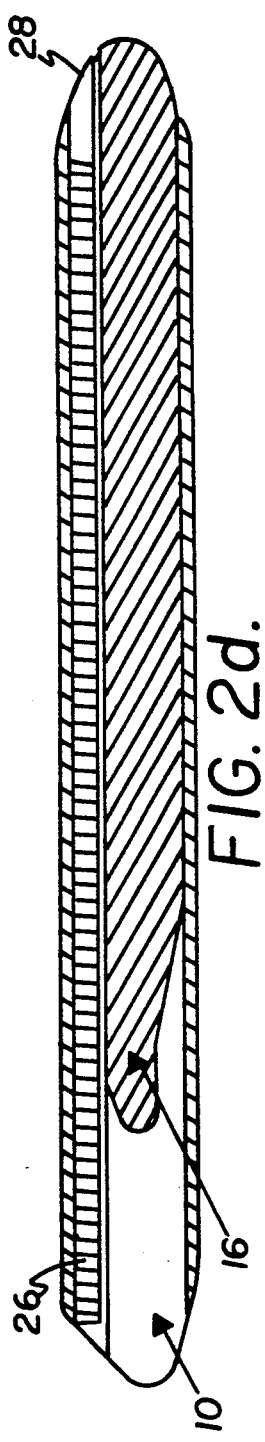

Reference will now be made in detail to the present preferred embodiments of the invention, an example of which is illustrated in the accompanying drawings. Identical or similar structure is identified by the same callouts. FIG. 1a shows a schematic representation of the side view of the assembled scalpel of the present invention with the surgical blade deployed, while FIG. 1b shows the designated A—A mechanical view thereof. Handle 10 has two windows, 12 and 14, located therein. The forward window 12 is elongated. Slide member 16 is adapted to hold surgical cutting blade 18, and further has a digit-engaging roughened portion 20 adapted to be engaged by a thumb or finger, and a raised, deformable latch member, 22. The handle is relieved 24 above window 12 in order to render roughened portion 20 more accessible to the operating digit. FIGS. 1c and 1d show a schematic representation of the top view and the designated B—B mechanical view of our scalpel, respectively. Illustrated is coil spring 26 and spring-engaging tab 28 which together transmit a continuous rearward force to slide member 16. Deformable latch member 22 is adapted to protrude through windows 12 and 14 when opposite said windows, while being deformable such that slide member 16 can be slidably moved through the handle cavity under the action of coil spring 26 or a digit in contact with roughened portion 20. Spring 26 forces said latch member against the rearward edge of either window 12 or 14 depending on in which window the latch member is located, when no force is applied to the roughened portion 20. FIG. 1 illustrates the latch member protruding through the elongated window and locking the scalpel in its open or actuated position. By depressing the deformable latch, the operator allows the slide member to automatically move further into the handle, thereby completely shielding surgical blade 18. Surgical blade 18 cannot therefore be accidentally deployed. FIG. 1e is a schematic representation of the rear view of the subject scalpel illustrating, in particular the cavity 30 in which slide 16 moves, the interior slot 32 in which coil spring 26 is located, deformable latch member 22, spring-engaging tab 28, and coil spring 26.

Tolerances and materials are selected such that the scalpel is stable in its operating or deployed mode yet is easily retracted. For surgical or other medical uses, materials must conform to Food and Drug Administration standards. For example, scalpels must be gamma-ray sterilizable and/or autoclavable. It is anticipated that the slide and handle portions of our scalpel will be made from dissimilar materials (metal and plastic, or two different plastics, as examples) chosen additionally for their moldability and for their relative coefficients of expansion and friction such that accurate tolerances can be maintained for operating stability, while maintaining ready relative motion and freedom from binding.

Figure 3:
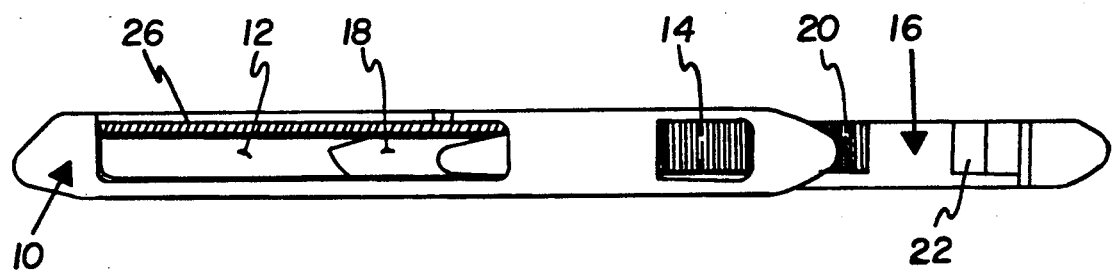
FIG. 3 shows a schematic representation of the assembled scalpel and illustrates that the slide/blade assembly may readily be removed for replacement, by depressing the deformable latch when located in the rearward handle window of the handle, and moving the slide out of the handle in the rearward direction.
Figure 4A:
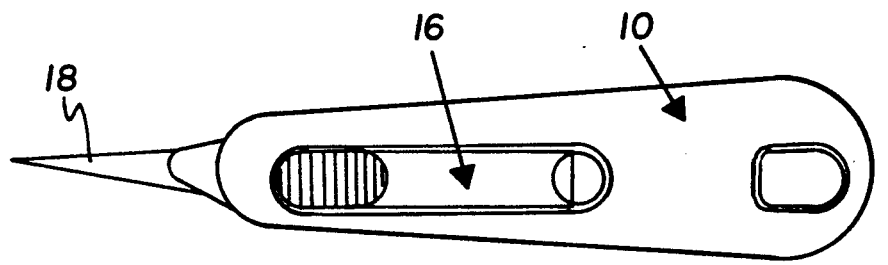
FIGS. 4a-c show a schematic representation the side, top, and rear views of a second embodiment of the present surgical scalpel adapted for making small incisions or punctures.
Figure 4C:
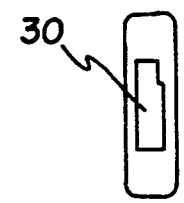
Figure 4B:
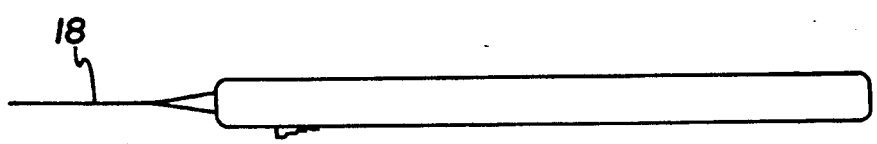

The retracted position is illustrated in FIG. 2 hereof. Identical views to those of FIG. 1 are presented. FIG. 3 illustrates the removal of slide member 16 from handle 10 through the rear opening therein for replacement of surgical blade 18 or of the entire slide member. FIG. 4 illustrates a second embodiment of our invention useful for making small or puncture incisions. This scalpel operates in a similar manner to that of the embodiment shown in FIGS. 1-3 hereof.

The foregoing description of two preferred embodiments of the invention have been presented for purposes of illustration and description. It is not intended to be exhaustive or to limit the invention to the precise form disclosed, and obviously many modifications and variations are possible in light of the above teaching. For example, it would be apparent to one having skill in the surgical arts after carefully studying the present disclosure that if there was no requirement to replace the slide member/cutting blade assembly, neither the rearward window in the handle nor the rear opening therein would be necessary. Moreover, another manner in which the slide member/cutting blade assembly, or the cutting blade alone, might be replaced would be to permit the handle sides to be reversibly detachable. Again, neither the rearward window nor the rearward opening in the handle would be necessary. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What we claim is:

1. A surgical scalpel having a retractable blade, comprising in combination:
   a. a generally flat, elongated handle member having a forward end and a rearward end, and further having two generally flat sides each having an interior flat recessed inner surface which together form an elongated cavity within said handle member extending substantially over the long dimension thereof and opening to the outside at the forward end of said handle member, a first side having two spaced-apart windows therethrough between the first flat recessed inner surface and the outside of said handle member, the window closest the forward end of said handle member being elongated along the long dimension of said handle member, and the second side having an interior elongated slot therein which terminates before reaching the forward end of said handle member and opening into the cavity toward the first side, the cavity and the interior slot in the second side both opening at the rearward end of said handle member;
   b. a surgical cutting blade;
   c. a flat, elongated slide member adapted to slidably move longitudinally through the cavity in said handle member, said slide member further being adapted to receive said surgical cutting blade, having a portion adapted to be engaged by and actuated by a digit through the elongated window in the first side of said handle member, having a raised, deformable latch member in the region of the end of said slide member away from the end thereof which is adapted to receive said surgical cutting blade and on the side thereof having the digit-engaging portion, and having a tab portion disposed in a direction perpendicular to the flat dimension thereof and away from the side thereof having the digit-engaging portion adapted to slidably move in the interior slot in the second side of said handle member; and
   d. coil spring means located within the interior slot in the second side of said handle member disposed generally along the long dimension thereof and adapted to continuously contact the tab portion of said slide member, thereby providing a force on said slide member directed toward the rearward end of said handle member;
   whereby said surgical cutting blade may be reversibly locked either entirely within said handle member or extend outside thereof through the opening therein in the forward end thereof for use in surgical procedures without continuous contact being required with the digit-engaging portion when said slide member is moved sufficiently toward the rearward end of said handle member to permit said raised, deformable latch member to extend through the window located toward the rearward end of said handle member and counteract the action of said coil spring means, or when said slide member is moved sufficiently toward the forward end of said handle member to permit said raised, deformable latch member to extend through the window closest to the forward end of said handle member and counteract the action of said coil spring means, respectively, a nd whereby said slide member may be reversibly removed for replacement thereof when said raised, deformable latch member is depressed when located in the window closest to the rearward end of said handle member and said slide member is moved away from the forward end thereof.

2. The surgical scalpel having a retractable blade as described in claim 1, wherein said slide member is adapted to removably receive said surgical cutting blade, whereby said surgical cutting blade may be replaced on said slide member.

3. A surgical scalpel having a retractable blade, comprising in combination:
   a. a generally flat, elongated handle member having a forward end and a rearward end, and further having two generally flat sides each having an interior flat recessed inner surface which together form an elongated cavity within said handle member extending substantially over the long dimension thereof and opening to the outside at the forward end of said handle member, a first side having an elongated window therethrough between the first flat recessed inner surface and the outside of said handle member, and the second side having an interior elongated slot therein which terminates before reaching the forward end of said handle member and opening into the cavity toward the first side;
   b. a surgical cutting blade;
   c. a flat, elongated slide member adapted to slidably move longitudinally through the cavity in said handle member, said slide member further being adapted to receive said surgical cutting blade, having a portion adapted to be engaged by and actuated by a digit through the elongated window in the first side of said handle member, having a raised, deformable latch member in the region of the end of said slide member away from the end thereof which is adapted to receive said surgical cutting blade and on the side thereof having the digit-engaging portion, and having a tab portion disposed in a direction perpendicular to the flat dimension thereof and away from the side thereof having the digit-engaging portion adapted to slidably move in the interior slot in the second side of said handle member; and
   d. coil spring means located within the interior slot in the second side of said handle member disposed generally along the long dimension thereof and adapted to continuously contact the tab portion of said slide member, thereby providing a force on said slide member directed toward the rearward end of said handle member;
   whereby said surgical cutting blade may be reversibly locked in a position extending outside of said handle member through the opening therein in the forward end thereof for use in surgical procedures without continuous contact being required with the digit-engaging portion when said slide member is moved sufficiently toward the forward end of said handle member to permit said raised, deformable latch member to extend through the window and counteract the action of said coil spring means.

4. The surgical scalpel having a retractable blade as described in claim 3, wherein the first side and the second side of said handle portion are reversibly separable such that said slide member may be replaced.

5. The surgical scalpel having a retractable blade as described in claim 4, wherein said slide member is adapted to removably receive said surgical cutting blade.

* * * * *